United States Patent [19]

Nguyen

[11] Patent Number: 5,189,194
[45] Date of Patent: Feb. 23, 1993

[54] PROCESS FOR PREPARATION OF HYDRIDO ORGANOOXYSILANES

[75] Inventor: Binh T. Nguyen, Midland, Mich.

[73] Assignee: Dow Corning Corporation, Midland, Mich.

[21] Appl. No.: 909,329

[22] Filed: Jul. 6, 1992

[51] Int. Cl.$^5$ ............................................. C07F 7/18
[52] U.S. Cl. ................................................ 556/471
[58] Field of Search ....................................... 556/471

[56] References Cited

U.S. PATENT DOCUMENTS 3,567,756 3/1971 Rothe .................................. 556/471

FOREIGN PATENT DOCUMENTS 3634524 4/1988 Fed. Rep. of Germany ...... 556/471
0011720 1/1976 Japan ................................. 556/471
1193739 6/1970 United Kingdom ............... 556/471

OTHER PUBLICATIONS

Miller et al., J. Am. Chem. Soc. 79: 5604-5606 (1957).

Primary Examiner—Paul F. Shaver
Attorney, Agent, or Firm—William F. Boley

[57] ABSTRACT

The present invention is a process for the preparation of hydrido organooxysilanes. The process comprises contacting a chlorosilane having at least one hydrogen atom bonded to the silicon atom with a anhydrous sodium organooxide. In a preferred embodiment, the process comprises adding the anhydrous sodium organooxide to the chlorosilane at a controlled rate. The process is conducted at a temperature within a range of about 0° C. to 70° C.

13 Claims, No Drawings

PROCESS FOR PREPARATION OF HYDRIDO ORGANOOXYSILANES

BACKGROUND OF INVENTION

The present invention is a process for the preparation of hydrido organooxysilanes. The process comprises contacting a chlorosilane having at least one hydrogen bonded to the silicon atom with a anhydrous sodium organooxide. In a preferred embodiment, the process comprises adding the anhydrous sodium organooxide to the chlorosilane at a controlled rate. The process is conducted at a temperature within a range of at about 0° C. to 70° C.

The hydrido organooxysilanes prepared by the present process are useful precursors for a variety of organooxysilanes. For example, the hydrido organooxysilanes can undergo hydrosilylation reactions with olefins without affecting the organooxy functionality on the silicon atom. The resultant silylated organic compounds can be used as bonded surface treatment for fibers and in polishes by subsequent hydrolysis of the organooxy functionality from the silicon atom.

Miller et al., J. Am. Chem. Soc 79:5604–5606, 1957, reported a process in which dibromosilane was reacted with sodium alkoxides to form the corresponding dialkoxysilane. Miller et al. reported that it was necessary to use an inert hydrocarbon solvent and a dry nitrogen atmosphere to prevent complete decomposition of the product during the course of the reaction. Miller et al. reported that monoorganobromosilane was also reactive in their process, with the bromine being replaced by an alkyloxy group. However, Miller et al. reported that monobromosilanes would not react in their process.

Therefore, unexpectly the present inventor has found that chlorosilanes having at least one hydrogen atom bonded to the silicon atom can react with sodium organooxides in the absence of a solvent to provide high yields of hydrido organooxysilanes. The yield of the present process is improved when the sodium organooxide is added to the chlorosilane at a controlled rate. The present process is further distinguished from that described by Miller et al. in that monochlorosilanes are reactive in the process.

SUMMARY OF INVENTION

The present invention is a process for the preparation of hydrido organooxysilanes. The process comprises contacting a chlorosilane having at least one hydrogen atom bonded to the silicon atom with a anhydrous sodium organooxide. In a preferred embodiment, the process comprises adding the anhydrous sodium organooxide to the chlorosilane at a controlled rate. The process is conducted at a temperature within a range of about 0° C. to 70° C.

DESCRIPTION OF INVENTION

The present invention is a process for preparing hydrido organooxysilanes. The process comprises:

(A) contacting a chlorosilane described by formula

with a sodium organooxide described by formula

at a temperature within a range of about 0° C. to 70° C. and (B) recovering a hydrido organooxysilane described by formula

where each R is independently selected from a group consisting of alkyls comprising one to 20 carbon atoms, cycloalkyls comprising four to 20 carbon atoms, alkenyls comprising two to 20 carbon atoms, alkyloxys comprising one to 20 carbon atoms, and aryls; $R^1$ is selected from a group consisting of alkyls comprising one to six carbon atoms and aryls: $a=0$, 1, or 2; $b=1$, 2, or 3; and $a+b=1$, 2, or 3.

Contacting the chlorosilane and sodium organooxide can be accomplished in standard reactors suitable for reacting chlorosilanes. The process can be run as a batch, semi-batch, or continuous type process. The process can be run, for example, in a continuous-stirred tank reactor. In a preferred embodiment, the sodium organooxide is added at a controlled rate to a reactor containing the chlorosilane. By "controlled rate," it is meant that the sodium organooxide is added to the process such that it can be quickly dispersed into the chlorosilane thereby minimizing localized high concentrations of the sodium organooxide within the chlorosilane. The optimal controlled rate will depend upon such factors as the volume of the chlorosilane and the efficiency of mixing.

The time required for contact of the chlorosilane with the sodium organooxide to form the hydrido organooxysilane will depend upon such factors as the temperature at which the present process is being conducted and the chemical compositions of the reactants. In general, contact times within a range of about 0.1 minute to five hours are considered useful. Preferred are contact times within a range of about one minute to one hour.

Chlorosilanes useful in the present process are described by formula (1). The chlorosilanes can have zero, one, or two substituents R, where each R is a radical independently selected from a group consisting of alkyls comprising one to 20 carbon atoms, cycloalkyls comprising four to 20 carbon atoms, alkenyls comprising two to 20 carbon atoms, alkyloxys comprising one to 20 carbon atoms, and aryls. The radical R can be, for example, methyl, ethyl, propyl, n-butyl, t-butyl, pentyl, cyclopentyl, cyclohexyl, cycloheptyl, vinyl, allyl, 1-methylvinyl, methoxy, ethoxy, phenyl, xylyl, or tolyl. Preferred are those chlorosilanes where R is an alkyl comprising one to six carbon atoms. The most preferred chlorosilanes are those having two substituents R and R is methyl.

The chlorosilanes useful in the present process can have one, two, or three hydrogen atoms bonded to each silicon atom. Preferred are those chlorosilanes having one hydrogen atom bonded to the silicon atom.

The chlorosilanes useful in the present process must have at least one chlorine atom bonded to the silicon atom and can have one, two, or three chlorine atoms bonded to the silicon atom. Preferred are those chlorosilanes having one chlorine atom bonded to the silicon atom.

Sodium organooxides useful in the present process are described by formula (2). The sodium organooxide has substituent $R^1$, where $R^1$ is selected from a group consisting of alkyls comprising one to six carbon atoms and aryls. The radical $R^1$ can be, for example, methyl, ethyl, propyl, butyl, tert-butyl, iso-butyl, pentyl, hexyl, and phenyl. Preferred is when $R^1$ is methyl.

In a preferred embodiment of the present process, the sodium organooxide and the chlorosilane are added to the process at about stoichiometric equivalence. By "stoichiometric equivalence," it is meant that one mole of sodium organooxide is added to the process for each mole of chlorine bonded to the chlorosilane added to the process. By "about stoichiometric equivalence," it is meant that the sodium organooxide is added to the process within a range of plus ten percent to minus ten percent stoichiometric equivalence. Lessor or greater mole ratios of sodium organooxide and chlorosilanes may be used in the process, but these may result in reduced yield of the desired hydrido organooxysilane.

The present process is conducted at a temperature within a range of about 0° C. to 70° C. Preferred is a temperature within a range of about 20° C. to 50° C. The temperature of the process can be controlled by standard means, for example, a heat transfer fluid present in a jacket or bath encompassing a portion of the reactor.

Hydrido organooxysilanes described by formula (3) are recovered from the present process. The hydrido organooxysilane can be recovered by standard methods for separating mixtures, for example, distillation. Recovery of the hydrido organooxysilane may include merely feeding the mixture containing the hydrido organooxysilane to another process or storing the mixture containing the hydrido organooxysilane for future use.

A preferred hydrido organooxysilane recovered from the present process is dimethylmethoxysilane.

The following examples are provided to illustrated the present invention. These examples are not intended to limited the scope of the present claims.

EXAMPLE 1

Sodium methoxide was added to dimethylchlorosilane to form dimethylmethoxysilane. The process was conducted in a 100 mL three-neck flask equipped with a thermometer, an addition funnel, and a magnetic stirring bar. The temperature of the flask was controlled by means of a water bath. The process was conducted by placing 25 ml (0.229 mol) of dimethylchlorosilane in the flask and slowly adding 12.39 g (0.229 mol) of solid anhydrous sodium methoxide to the dimethylchlorosilane by means of the addition funnel. Addition of the sodium methoxide took about 0.45 hour. Temperature of the flask content was kept at about 31° C. by means of the water bath. The flask content was distilled using a Vigreaux column at 35° C. to 36° C. to yield 19.1 g of clear liquid. The clear liquid was analyzed by gas chromatography (GC) using a mass spectrometer (MS) as a detector and found to comprise about 93.2% dimethylmethoxysilane, as evidenced by the area under the GC/MS trace.

EXAMPLE 2

Dimethylchlorosilane was added to sodium methoxide to form dimethylmethoxysilane. The process was conducted similar to that described in Example 1. A sample of anhydrous sodium methoxide weighing 12.39 g (0.229 mol) was loaded into the flask. Then, 25 mL (0.229 mol) of dimethylchlorosilane was slowly added to the flask over a period of 0.5 hour. The temperature of the flask content was controlled at about 31° C. After all the dimethylchlorosilane was added to the flask, the resultant mixture was heated to reflux for 0.5 hour. The resultant mixture was distilled to remove low boiling materials. The total weight of the clear liquid distillate was 17 g. The clear liquid distillate was analyzed by GC/MS, as previously described, and found to comprise about 23.7% dimethylmethoxysilane and about 59% dimethyldimethoxysilane.

I claim:

1. A process to prepare hydrido organooxysilanes, the process comprising:

(A) contacting a chlorosilane described by formula $$R_aH_bSiCl_{4-a-b}$$

with a sodium organooxide described by formula $$NaOR^1$$

at a temperature within a range of about 0° C. to 50° C., and (B) recovering a hydrido organooxysilane described by formula $$R_aH_bSi(OR^1)_{4-a-b},$$

where each R is independently selected from a group consisting of alkyls comprising one to 20 carbon atoms, cycloalkyls comprising four to 20 carbon atoms, alkenyls comprising two to 20 carbon atoms, alkyloxys comprising one to 20 carbon atoms, and aryls; $R^1$ is selected from a group consisting of alkyls comprising one to six carbon atoms and aryls; a=0, 1, or 2; b=1, 2, or 3; and a+b=1, 2, or 3.

2. A process according to claim 1, where the sodium organooxide is added at a controlled rate to a reactor containing the chlorosilane.

3. A process according to claim 1, where contact time of the sodium organooxide with the chlorosilane is within a range of about one minute to one hour.

4. A process according to claim 1 where R is an alkyl comprising one to six carbon atoms.

5. A process according to claim 1, where R is methyl.

6. A process according to claim 1, where a=2.

7. A process according to claim 1, where b=1.

8. A process according to claim 1, where a+b=3.

9. A process according to claim 1, where $R^1$ is methyl.

10. A process according to claim 1, where the sodium organooxide and the chlorosilane are added to the process at about stoichiometric equivalence.

11. A process according to claim 1, where the temperature is within a range of about 20° C. to 50° C.

12. A process according to claim 1, where the hydrido organooxysilane is dimethylmethoxysilane.

13. A process according to claim 1, where the sodium organooxide is added at a controlled rate to a reactor containing the chlorosilane, the sodium organooxide and the chlorosilane are added to the process at about stoichiometric equivalence, contact time of the sodium organooxide with the chlorosilane is within a range of about one minute to one hour, R is an alkyl comprising one to six carbon atoms, a=2, b=1, and the temperature is within a range of about 20° C. to 50° C.

* * * * *